United States Patent
Schaldach et al.

(10) Patent No.: US 6,524,256 B2
(45) Date of Patent: Feb. 25, 2003

(54) IMPLANTABLE MEASURING DEVICE, PARTICULARLY A PRESSURE MEASURING DEVICE FOR DETERMINING THE INTRACARDIAL OR INTRALUMINAL BLOOD PRESSURE

(75) Inventors: Max Schaldach, deceased, late of Erlangen (DE), by Max Schaldach, Jr., legal representative; Bernhard Döllgast, Erlangen (DE); Gregor Niewalda, Erlangen (DE)

(73) Assignee: Biotronik Mess-und Therapiegeraete GmbH & Co. Ingenieürbuero Berlin, Berlin (DE)

( * ) Notice: Subject to any disclaimer, the term of this patent is extended or adjusted under 35 U.S.C. 154(b) by 0 days.

(21) Appl. No.: 09/909,987

(22) Filed: Jul. 23, 2001

(65) Prior Publication Data

US 2002/0028999 A1 Mar. 7, 2002

(30) Foreign Application Priority Data

Jul. 22, 2000 (DE) .......................... 100 35 774
Sep. 13, 2000 (DE) .......................... 100 45 275

(51) Int. Cl.$^7$ ................................ A61B 5/02
(52) U.S. Cl. ................. 600/486; 600/485; 600/488
(58) Field of Search ................. 600/486, 485, 600/481, 483, 488, 508; 607/9, 23, 27, 31

(56) References Cited

U.S. PATENT DOCUMENTS

| 4,509,947 | A | | 4/1985 | Lattin |
| 4,628,928 | A | * | 12/1986 | Lowell .................. 600/486 |
| 4,698,058 | A | | 10/1987 | Greenfeld et al. |
| 5,889,212 | A | * | 3/1999 | Guthrie et al. .............. 600/485 |

FOREIGN PATENT DOCUMENTS

| DE | 22 31 491 A1 | 1/1973 |
| DE | 27 08 607 A1 | 9/1977 |
| DE | 83 22 149 U1 | 3/1984 |

* cited by examiner

Primary Examiner—Kevin Shaver
Assistant Examiner—Navin Natnithithadha
(74) Attorney, Agent, or Firm—Browdy and Neimark, P.L.L.C.

(57) ABSTRACT

An implantable measuring device includes a catheter-like main body that can be positioned in a body cavity. The main body has a pressure-sensitive sensor thereon and a signal line is coupled to the sensor. The signal line transmits measuring signals generated by the sensor and corresponding to the detected pressure to a signal evaluation unit. A cleaning element is coupled to the sensor. The cleaning element is in the form of a piezoelectric actuator that can be set to vibrate by electrical excitation. The vibrations of the cleaning unit are transferable to the sensor for the removal of deposits.

11 Claims, 1 Drawing Sheet

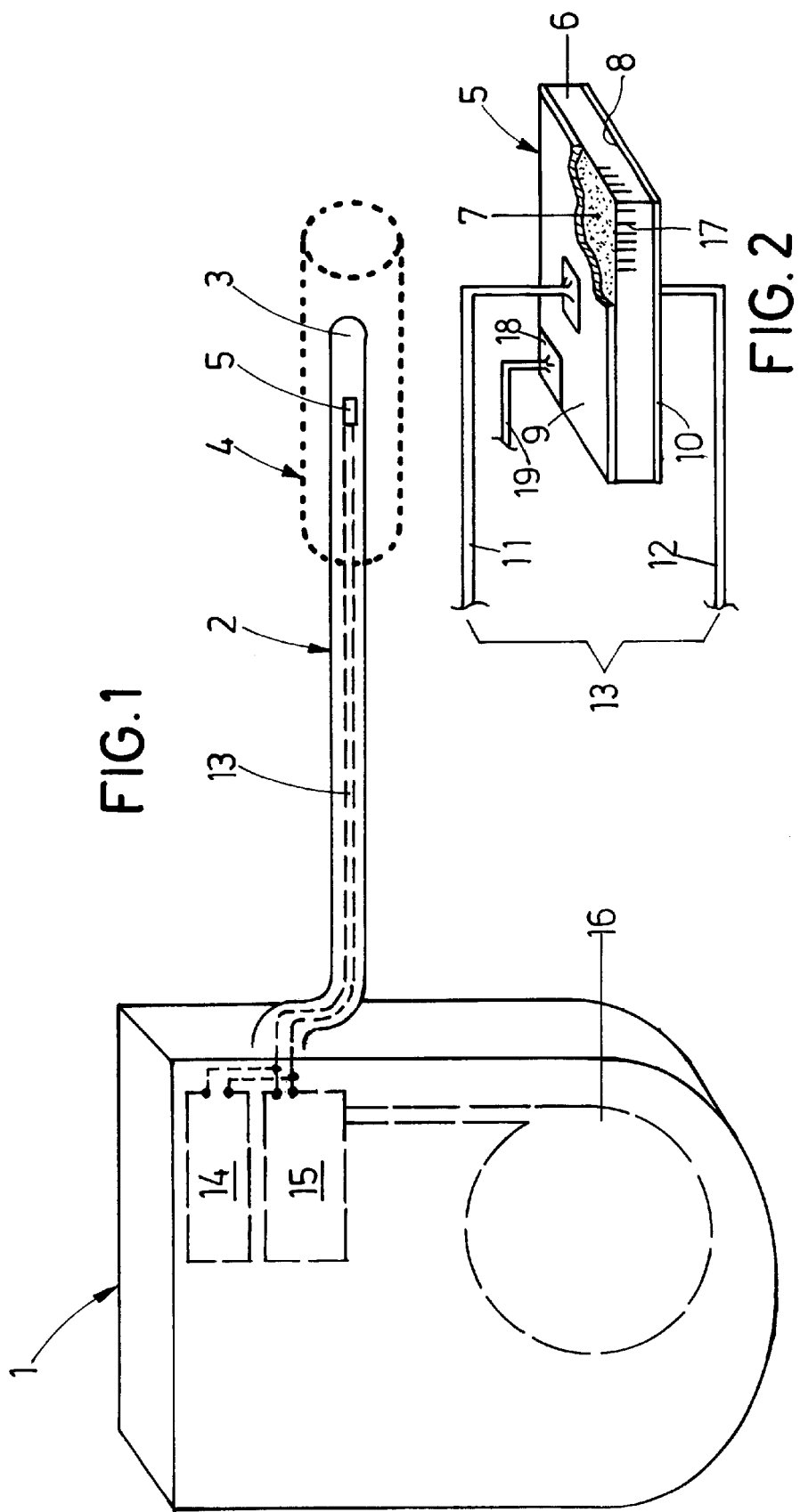

IMPLANTABLE MEASURING DEVICE, PARTICULARLY A PRESSURE MEASURING DEVICE FOR DETERMINING THE INTRACARDIAL OR INTRALUMINAL BLOOD PRESSURE

BACKGROUND OF THE INVENTION

1. Field of the Invention

The present invention is concerned with an implantable measuring device, particularly a measuring device for determining the intacardial or intraluminal blood pressure.

2. Background Art

Regarding the background of the invention it can be stated, based on the example of an implantable pressure measuring device, that measuring the intracardial or intraluminal—e.g., arterial—blood pressure is of importance in pacemaker therapy. The average arterial blood pressure for example, is a physiological parameter with the aid of which the stimulation rate of a rate adaptive cardiac pacemaker is adaptable. The intracardial pressure curve, as a further example for the application of pressure measurements, can provide information regarding the activity of the heart valves, the contraction sequence of the heart, and its contractility. In optimal circumstances physiological parameters of this type will be monitored permanently, as they may be continually needed as input parameters for a whole variety of applications.

A permanent operation of implantable pressure measuring devices of this type, such as electromechanical pressure measuring catheters, for example, is not practically feasible at this time as the sensor surfaces will gradually become covered due to the clot formation coagulation and endothelialization occurring on the same because of their constant actuation by the blood flow. This causes their sensitivity to be significantly reduced. This also holds true, for example, for optical sensors that are able to determine the blood oxygen saturation by measuring the amplitude ratio of two peaks in the infrared radiation band, the measuring properties of which ate also significantly deteriorated by the above-mentioned covering processes. For the above reasons implantable measuring sensors and especially pressure sensors are thus used only temporarily.

Measures to eliminate impurities caused by the blood flow arc already known from the prior art in the general context of intracorporally implanted catheters. U.S. Pat. No. 4,698, 058 for example, reveals a perfusion catheter, the fluid-carrying lumen of which is cleaned by means of ultra-sound. The sound waves are transmitted via an additional lumen that houses the inner catheter tube with the lumen that is to be cleaned. However, perfusion catheters are generally implanted only temporarily. The impurities that are deposited in its lumen are primarily due to the various chemical or blood-containing fluids that are routed through the catheter in both directions.

U.S. Pat. No. 4,509,947 reveals the cleaning of an implanted medication infusion pump by means of ultra-sound. However, this method does not serve to remove deposits caused by the contact of the infusion pump wit body fluids, but rather to remove crystallization that might occur from the medication reservoir.

The ultrasound cleaning devices according to the above printed publications obviously do not pertain to the problems of blood-generated impurities collecting on permanently implanted catheters. These printed publications, therefore, merely constitute technological background.

The present invention is now based on the object of equipping an implantable measuring device in such a way that it can be permanently positioned inside a body cavity that transports or contains a body medium that results in removal of deposits on the measuring device sensor.

This object is met with by the invention, which provides for a cleaning element that is coupled to the sensor is provided in the form of a piezoelectric, preferably piezoceramic actuator, which can be set in vibrations by electrical excitation via supply lines. These vibrations are conveyed to the sensor, setting the same in mechanical oscillations and thus removing the deposits. This cleaning process may be performed in regular intervals or as needed. The frequency and amplitude of the vibration signal may similarly also either be predetermined or opted automatically based on the degree of impurities or effect of the cleaning. The degree of impurities or effect of the cleaning may be determined based on the electrical, optical or mechanical properties of the measuring sensor.

Thin, block-shaped or discoid plate elements composed of piezoceramics, the large faces of which are at least partially covered with electrically conducting contact areas for connecting the supply lines, have proven to be the preferred embodiment for the actuator of the cleaning element. An actuator of this type then preferably lies flat against the sensor that is to be cleaned so that the most optimal transfer of the cleaning vibrations can take place.

Since primarily piezoceramic elements are used as the pressure sensitive sensors in pressure measuring catheters per se, a particularly preferred embodiment of the invention provides for a pressure sensitive sensor and actuator to be formed jointly by a uniform piezoceramic plate element. The signal line and supply line may then correspondingly also be formed by a single common pair of leads that is connected both to the measuring signal evaluation unit for the pressure measurement as well as to a control circuit for actuating the vibration of the plate element.

According to preferred embodiments of the invention, in order to optimize the cleaning effect, provision is made for th: vibration frequency of the actuator to be matched to its self-resonant frequency in its longitudinal or thickness direction. The actuator may Evermore be provided with micro-channels for generating micro flows of gas bubbles or fluid. These micro-channels, which act like nobles, operate according to the same method of operation as the print head of an ink jet printer and thus do not require any detailed explanation.

Lastly, for an optimized energy supply to the implantable measuring device with respect to a ideally unlimited service life, the inductive input of the electrical energy required to generate the actuator vibrations may be provided via an antenna. The latter may be located in the implant in its so-called header, in the supply line to the sensor, or on the sensor itself.

Further characteristics, details and advantages of the invention will become apparent from the following description in which an exemplary embodiment will be explained in more detail based on the appended drawings.

BRIEF DESCRIPTION OF THE DRAWINGS

FIG. 1 shows a schematic, perspective illustration of a permanently implantable cardiac pacemaker with a pressure measuring catheter ending from the same, and FIG. 2 shows a schematic perspective illustration of a piezoceramic plate element as it is used as a self-cleaning pressure sensor in the catheter according to FIG. 1.

DESCRIPTION OF THE PREFERRED EMBODIMENT

In FIG. 1 a cardiac pacemaker 1 can be seen that can be permanently implanted into a patient's body. It is of the type of a rate adaptive pacemaker, the stimulation rate of which is adjusted using the average arterial blood pressure as the physiological parameter. In order to determine the same, the cardiac pacemaker 1 has coupled to it a catheter 2, the distal end 3 of which can be positioned in the artery 4 indicated by a dotted line. A self-cleaning pressure sensor 5 that detects the prevailing pressure in the artery 4, is disposed on the distal end 3 of the catheter 2.

As is apparent from FIG. 2, this pressure sensor 5 comprises a thin block-shaped piezoceramic plate element 6, the two large faces 7, 9 of which are coated with a contact layer 9, 10, for example of silver. Each of these contact layers 9, 10 is brought into contact with one conducting wire 11, 12 of a pair of leads 13 (FIG. 1) by means of soldering, with the pair of leads being connected to a measuring signal evaluation unit 14 on one hand and a control circuit 11 for generating a high-frequency alternating voltage between the two conducting wires 11, 12 on the other had.

The piezo plate element 6—as previously mentioned—serves as a pressure sensor on one hand, as the pressure exerted onto the plate clement results in a representative voltage between the two contact layers 9, 10, which can be registered by the measuring signal evaluation unit 14 and converted into a corresponding pressure value At the same time the piezoceramic plate clement 6 also serves as a cleaning element in the form of a piezoceramic actuator that is set in vibrations by the high-frequency alternating voltage made available by the control circuit 15, said vibrations ensuring the removal of deposits on the plate element 6. The energy for this high-frequency alternating voltage is transferred to the pacemaker 1 inductively from outside through an electromagnetic alternating field that is received by the antenna 16, which is coupled to the control circuit 15 and located in the pacemaker 1. The frequency of the alternating voltage lies within the range of the self-resonant frequency of the piezoceramic plate element 6 and thus in the order of magnitude of kHz. A particularly intensive oscillation excitation of the plate element 6 is made possible by adapting the excitation frequency to the self-resonant frequency of the plate element 6. To simplify the actuation and provide for an adaptive guidance of the oscillation excitation, a point of the contact layer 9, 10 may be designed as a feedback electrode 18, the signal of which is supplied to the control circuit 15 via an additional line 19 (FIG. 2). This results in the same optimization of the cleaning effect as the design of the plate element 6 in the form of a multi-layer construction.

In a further improvement, the piezoceramic plate element 6 may—as indicated in FIG. 2—be provided with microchannels 17 that additionally provide for a pulse-like ejection of gas bubbles or fluid jets during an oscillation excitation of the plate element 6. This has an additional significant removal effect on deposits on the plate element 6.

Preliminary tests with piezoceramic actuators in the form of plate elements with a surface area of 5 mm×5 mm and a respective thickness of 0.2 mm, 0.5 mm and 1 mm, have resulted in estimated planar or longitudinal self-resonant frequencies between approximately 10 kHz and 15 kHz in two different ceramic materials. These plate elements that were provided with full-surface silver electrodes and soldered-on enameled copper wire, were each stored in bovine blood at 37° C. for 15 minutes, 1 hour, 24 hours and 4 days, respectively. Depending on the storage time and type of material, this resulted in deposits in the form of coagulation layers, to fibrinogenesis and thrombogenesis on the plates For self-cleaning purposes, these plates were subsequently actuated with a sinus voltage in the range of the above frequencies and an amplitude of 5 volts to 15 volts. The results showed that the vibration time whereby an effective cleaning could be attained under the described circumstances lasted between 30 seconds and 300 seconds, depending on the type of the piezo element and its storage time. The elements wit a layer thickness of 0.2 mm revealed better properties compared to the thicker elements, namely primarily shorter cleaning times, which is likely due to the higher field strength based on the lesser thickness.

In the above piezoceramic actuators selected for the preliminary tests, the self-resonant thickness frequencies arc within the range of approximately 2 MHz to 10 MHz. When tho actuator is excited in this frequency range, additional cavitation effects may be expected, which contribute to an intensive cleaning of the actuators.

What is claimed is:

1. An implantable measuring device, comprising
a main body (2) that can be positioned in a given body cavity (4),
a measurement-sensitive sensor (5) on the main body (2),
a signal line (13) coupled to the sensor for transmitting to a measuring signal evaluation unit (15) of a measuring device the measuring signals generated by the sensor (5) corresponding to a detected measuring value, and
a cleaning element (6) coupled to the sensor (5) in the form of a piezoelectric actuator that can be set in vibration by electrical excitation via supply lines (13), said vibration being transferable to the sensor (5) for removal of deposits.

2. A measuring device according to claim 1, wherein the actuator is a thin plate element (6) of piezoceramics with large faces (7, 8) which are at least partially covered with electrically conducting contact areas (9, 10) for the supply lines (13).

3. A measuring device according to claim 2, wherein a feedback electrode (18) that is connected to a control circuit (15) for a vibration actuation of the plate element (6) is partitioned off on at least one contact area (9).

4. A measuring device according to claim 1, wherein the actuator lies flat against the sensor.

5. A measuring device according to claim 1, wherein the sensor, which is designed as a pressure sensor, and the actuator are jointly formed by a uniform piezoceramic plate element (6).

6. A measuring device according to claim 5, wherein the signal line and the supply line are formed by a common pair of leads (13) at is connected to the measuring signal evaluation unit (14) and to a control circuit (15) for a vibration actuation of the piezoceramic plate element (6).

7. A measuring device according to claim 1, wherein a vibration frequency of the actuator (6) corresponds to a self-resonant frequency.

8. A measuring device according to claim 1, wherein the actuator (6) is provided with microchannels (17) for generating micro flows of gas or fluid.

9. A measuring device according to claim 1, wherein an energy required to generate the vibrations of the actuator (6) can be coupled-in inductively via an antenna (16).

10. A measuring device in accordance with claim 1 which is a pressure measuring device for determining an intracardial or intraluminal blood pressure.

11. A measuring device in accordance with claim 1, wherein said main body is catheter-like.

* * * * *